(12) United States Patent
Mohammadi Purfard

(10) Patent No.: US 11,389,558 B2
(45) Date of Patent: Jul. 19, 2022

(54) TRANSPARENT WOUND DRESSINGS CONTAINING THYMOL NANOPARTICLES

(71) Applicant: Amin Mohammadi Purfard, Tehran (IR)

(72) Inventor: Amin Mohammadi Purfard, Tehran (IR)

(*) Notice: Subject to any disclaimer, the term of this patent is extended or adjusted under 35 U.S.C. 154(b) by 92 days.

(21) Appl. No.: 17/019,231

(22) Filed: Sep. 12, 2020

(65) Prior Publication Data

US 2020/0405904 A1 Dec. 31, 2020

Related U.S. Application Data

(60) Provisional application No. 62/901,823, filed on Sep. 18, 2019.

(51) Int. Cl.
| | |
|---|---|
| *A61L 15/32* | (2006.01) |
| *A61L 15/24* | (2006.01) |
| *A61L 15/22* | (2006.01) |
| *A61L 15/28* | (2006.01) |

(52) U.S. Cl.
CPC .............. *A61L 15/32* (2013.01); *A61L 15/225* (2013.01); *A61L 15/24* (2013.01); *A61L 15/28* (2013.01); *A61L 2300/216* (2013.01); *A61L 2300/802* (2013.01)

(58) Field of Classification Search
CPC ...... A61K 47/42; A61K 47/38; A61K 9/0014; A61K 47/6957; A61L 26/0038
See application file for complete search history.

(56) References Cited

U.S. PATENT DOCUMENTS

| | | | |
|---|---|---|---|
| 2005/0163818 A1* | 7/2005 | Sung | A61L 27/54 424/423 |
| 2016/0007594 A1* | 1/2016 | Li | A01N 31/16 514/731 |
| 2019/0060512 A1* | 2/2019 | Phillips | A61L 15/32 |

OTHER PUBLICATIONS

To Muzzarelli et al., Marine Drugs, 2015, 13, 7314-7338.*
Aldana et al. Materials Chemistry and Physics, 134, 2012, 317-324.*
Sarem et al., Carbohydrate Polymers, 93, 2013, 635-643.*
Kaihara et al. Colloids and Surfaces B, 85, 2011,343-348.*

* cited by examiner

*Primary Examiner* — Kyle A Purdy
(74) *Attorney, Agent, or Firm* — Bajwa IP Law Firm; Haris Zaheer Bajwa

(57) ABSTRACT

A wound dressing including a hydropolymer matrix cross-linked with genipin and a plurality of thymol nanoparticles loaded into the hydropolymer matrix. The plurality of thymol nanoparticles has a concentration between 0.01 wt. % and 1 wt. % of dry weight of the wound dressing. The hydropolymer matrix includes gelatin, chitosan, polyvinylpyrrolidone (PVP), and carboxymethyl cellulose (CMC).

19 Claims, 3 Drawing Sheets

| Day<br>Patient | Day 0 | Day 15 | Day 30 |
|---|---|---|---|
| Patient 1 with a grade-3 bedsore |  |  |  |
| Patient 2 with a grade-3 bedsore |  |  |  |
| Patient 3 with a bedsore |  |  |  |
| Patient 4 with a cavity wound |  |  |  |

TRANSPARENT WOUND DRESSINGS CONTAINING THYMOL NANOPARTICLES

CROSS-REFERENCE TO RELATED APPLICATION

This application claims the benefit of priority from U.S. Provisional Patent Application Ser. No. 62/901,823, filed on Sep. 18, 2019, and entitled "POLYMERIC DRESSING BASED ON ZATARIA MULTIFLORA NANOPARTICLES," which is incorporated herein by reference in its entirety.

TECHNICAL FIELD

The present disclosure generally relates to wound dressings, particularly to wound dressings containing herbal extracts, and more particularly to wound dressings containing thymol nanoparticles.

BACKGROUND

Wounds occur when integrity of any tissue is damaged following injury to skin or underlying tissues. Wound healing is a complex biological process that results in regeneration of damaged tissues in presence of a suitable environment. Wound dressings by providing a proper environment around wounds may aid in accelerating a wound healing process. Ideal wound dressings have several characteristics, such as absorbing wound's secretions, creating a humid environment around an injured site, allowing gases to be exchanged between wounds and their environments, and preventing wound infections while being non-toxic and allergic. Conventional wound dressings may be made up of cotton yarns without any active substances, such as antibacterial agents, topical pain relievers, and compounds that promote healing of wounds. Also, antibacterial wound dressings containing silver nanoparticles have been raised concerns over increased concentrations of silver in environments and food chains, which in turn leads to other toxicities.

Moreover, conventional wound dressings causes several problems for users, such as possibility of contamination and development of secondary infections at sites of wounds, impossibility of observing wounds to inspect injury sites due to non-transparency of conventional wound dressings, adhesion of wound's secretions to wound dressings causing severe pain accompanied by bleeding and removal of newly-generated cells on injury sites, and putting wounds in contact with air which dries wounds and results in creating rashes and scars.

Hence, there is a need for transparent and effective antimicrobial wound dressings containing biodegradable active agents for promoting wound healing without any toxicity. Also, there is a need for ready-to-use wound dressings for treating a wide range of wounds, such as burns, bedsores, and diabetic ulcers without drying wounds.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary wound dressing including a hydropolymer matrix crosslinked with genipin and a plurality of thymol nanoparticles loaded into the hydropolymer matrix. In an exemplary embodiment, a plurality of thymol nanoparticles may have a concentration between about 0.01 wt. % and about 1 wt. % of dry weight of the wound dressing. In an exemplary embodiment, each of the plurality of thymol nanoparticles may have a particle size between about 20 nm and about 30 nm. In an exemplary embodiment, genipin may have a concentration between about 1 wt. % and about 20 wt. % of dry weight of the wound dressing.

In an exemplary embodiment, the hydropolymer matrix may include gelatin, chitosan, polyvinylpyrrolidone (PVP), and carboxymethyl cellulose (CMC). In an exemplary embodiment, gelatin may have a concentration between about 10 wt. % and about 90 wt. % of dry weight of the wound dressing. In an exemplary embodiment, chitosan may have a concentration between about 0.1 wt. % and about 30 wt. % of dry weight of the wound dressing. In an exemplary embodiment, PVP may have a concentration between about 0.1 wt. % and about 10 wt. % of dry weight of the wound dressing. In an exemplary embodiment, CMC may have a concentration between about 0.1 wt. % and about 35 wt. % of dry weight of the wound dressing.

In an exemplary embodiment, an exemplary wound dressing may further include at least one of adenosine triphosphate (ATP), vitamin C, honey, and glycerin. In an exemplary embodiment, ATP may have a concentration between about 0.0001 wt. % and about 0.1 wt. % of dry weight of the wound dressing. In an exemplary embodiment, vitamin C may have a concentration between about 0.001 wt. % and about 1 wt. % of dry weight of the wound dressing. In an exemplary embodiment, honey may have a concentration between about 5 wt. % and about 25 wt. % of dry weight of the wound dressing. In an exemplary embodiment, glycerin may have a concentration between about 5 wt. % and about 25 wt. % of dry weight of the wound dressing.

In an exemplary embodiment, an exemplary wound dressing may further include an additive. In an exemplary embodiment, the additive may include at least one of a chamomile extract, a calendula extract, a peppermint extract, olive oil, and an aloe vera extract. In an exemplary embodiment, a chamomile extract may have a concentration up to about 15 wt. % of dry weight of the wound dressing. In an exemplary embodiment, an aloe vera extract may have a concentration between about 0.1 wt. % and about 25 wt. % of dry weight of the wound dressing.

In an exemplary embodiment, a calendula extract may have a concentration up to about 15 wt. % of dry weight of the wound dressing. In an exemplary embodiment, a peppermint extract may have a concentration up to about 1 wt. % of dry weight of the wound dressing. In an exemplary embodiment, olive oil may have a concentration up to about 15 wt. % of dry weight of the wound dressing. In an exemplary embodiment, an exemplary wound dressing may further include water with a weight ratio of at least about 80 wt. % of total weight of the wound dressing.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
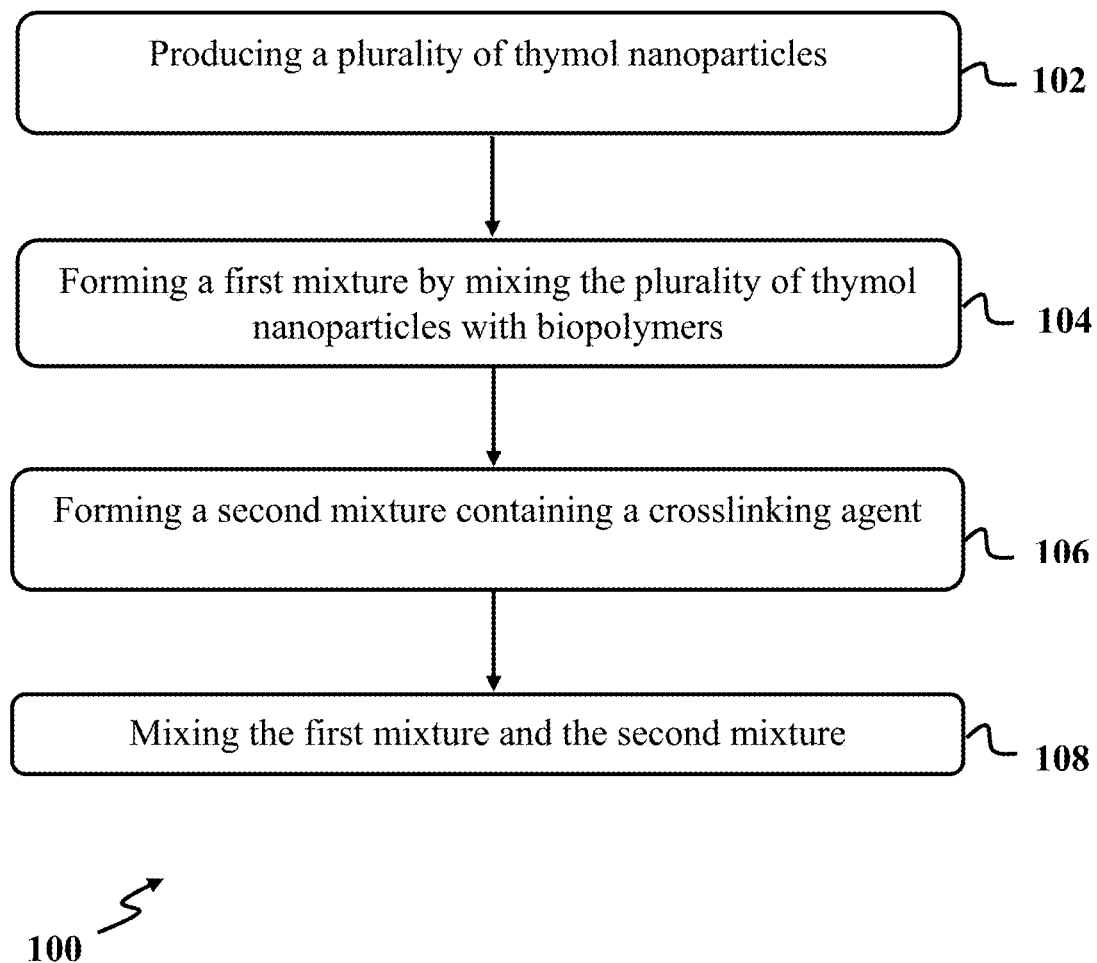
FIG. 1 illustrates a flowchart of an exemplary method for fabricating an exemplary wound dressing containing a plurality of thymol nanoparticles, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The present disclosure describes an exemplary transparent wound dressing containing natural biopolymers, thymol nanoparticles as an antimicrobial and antioxidant agent, and various additives. An exemplary wound dressing may be designed with different formulations for treating different types of wounds, such as burns, bedsores, and diabetic ulcers. An exemplary wound dressing may be safe without any side effects (due to biocompatibility of the compounds used in an exemplary wound dressing). In an exemplary embodiment, an exemplary wound dressing may be used for treating grade one (1) and grade two (2) burn wounds, grade one (1) to grade three (3) bedsores, diabetic ulcers, sunburns, skin grafts, and covering sutures. An exemplary wound dressing may include biodegradable natural material and herbal extracts which accelerate a wound healing process without any toxicity. In an exemplary embodiment, an exemplary wound dressing may be ready-to-use without any need for a preparation process before applying to wounds due to a hydrogel structure of an exemplary wound dressing containing water with a weight ratio of at least 80 wt. % of total weight of the wound dressing.

In an exemplary embodiment, an exemplary wound dressing may include a hydropolymer matrix crosslinked with genipin and a plurality of thymol nanoparticles loaded into the hydropolymer matrix. In the present disclosure, "hydropolymer matrix" may refer to a matrix containing hydrophilic polymers. In an exemplary embodiment, a plurality of thymol nanoparticles may have a concentration between about 0.01 wt. % and about 1 wt. % of dry weight of the wound dressing. In an exemplary embodiment, a plurality of thymol nanoparticles may serve as an antioxidant and antibacterial agent. In an exemplary embodiment, a plurality of thymol nanoparticles may be obtained by forming thymol particles through purifying thymol from an essence (essential oil) of *Zataria multiflora* and nanosizing the thymol particles.

In an exemplary embodiment, each of the plurality of thymol nanoparticles may have a particle size between about 20 nm and about 30 nm. In an exemplary embodiment, a plurality of thymol nanoparticles may have a larger surface area in comparison to surface areas of thymol microparticles; therefore, the larger surface area of the plurality of thymol nanoparticles may lead to more contact of bacteria with thymol and higher antibacterial effect of the exemplary wound dressing compared to wound dressing containing thymol microparticles.

In the present disclosure, "dry weight of the wound dressing" may refer to weight of the wound dressing dried at a temperature of about 105° C. In an exemplary embodiment, the hydropolymer matrix may include gelatin, chitosan, polyvinylpyrrolidone (PVP), and carboxymethyl cellulose (CMC). In an exemplary embodiment, gelatin may have a concentration between about 10 wt. % and about 90 wt. % of dry weight of the wound dressing. In an exemplary embodiment, chitosan may have a concentration between about 0.1 wt. % and about 30 wt. % of dry weight of the wound dressing. In an exemplary embodiment, PVP may have a concentration between about 0.1 wt. % and about 10 wt. % of dry weight of the wound dressing. In an exemplary embodiment, CMC may have a concentration between about 0.1 wt. % and about 35 wt. % of dry weight of the wound dressing.

In an exemplary embodiment, the hydropolymer matrix may be formed by crosslinking gelatin, chitosan, PVP, and CMC biopolymers using genipin as a crosslinking agent. In an exemplary embodiment, genipin may have a concentration between about 1 wt. % and about 20 wt. % of dry weight of the wound dressing. In an exemplary embodiment, genipin may be obtained by purifying an extract of garden-variety jasmine (*Gardenia jasminoides*). In an exemplary embodiment, a plurality of nanocapsules may be formed in the hydropolymer matrix responsive to crosslinking polymeric strands of gelatin, chitosan, PVP, and CMC biopolymers with each other. In an exemplary embodiment, the plurality of nanocapsules may trap different compounds of an exemplary wound dressing such as thymol nanoparticles and may provide a controlled release for these different compounds.

In an exemplary embodiment, crosslinking gelatin, chitosan, PVP, and CMC biopolymers may form a crosslinked three-dimensional network with improved physicomechanical properties such as high water retention compared to physicomechanical properties of a non-crosslinked three-dimensional network of biopolymers. In an exemplary embodiment, the exemplary wound dressing may keep water in the hydrophilic three-dimensional network of the hydropolymer matrix which may help in preserving moisture at wound sites, reducing inflammation, eliminating adhesion to the wound, and replacing the wound dressing in a painless condition. In an exemplary embodiment, biopolymers of the exemplary hydropolymer matrix such as gelatin may make the exemplary wound dressing transparent which facilitates monitoring wound sites, tracking the healing process.

In an exemplary embodiment, an exemplary wound dressing may further include at least one of adenosine triphosphate (ATP), vitamin C, honey, and glycerin. In an exemplary embodiment, ATP may have a concentration between about 0.0001 wt. % and about 0.1 wt. % of dry weight of the wound dressing. In an exemplary embodiment, an exemplary wound dressing may include ATP because ATP may aid in supplying energy for enzymes and organs involved in a wound healing process. In an exemplary embodiment, vitamin C may have a concentration between about 0.001 wt. % and about 1 wt. % of dry weight of the wound dressing. In an exemplary embodiment, an exemplary wound dressing may include vitamin C because vitamin C may aid in increasing collagen formation and improving a wound healing process. In an exemplary embodiment, an exemplary wound dressing may encapsulate vitamin C in the plurality of nanocapsules which may control the release of vitamin C into wound sites.

In an exemplary embodiment, honey may have a concentration between about 5 wt. % and about 25 wt. % of dry weight of the wound dressing. In an exemplary embodiment, an exemplary wound dressing may include honey because honey may serve as a nutritional agent for reconstructing damaged tissue. In an exemplary embodiment, glycerin may have a concentration between about 5 wt. % and about 25 wt. % of dry weight of the wound dressing. In an exemplary embodiment, an exemplary wound dressing may include glycerin for providing flexibility in the exemplary wound dressing.

In an exemplary embodiment, an exemplary wound dressing may further include an additive. In an exemplary embodiment, the additive may include at least one of a chamomile extract, an aloe vera extract, a calendula extract, a peppermint extract, and olive oil. In an exemplary embodiment, the additive may include at least one of menthol, carvacrol, and gamma-terpinene. In an exemplary embodiment, a chamomile extract may have a concentration up to about 15 wt. % of dry weight of the wound dressing. In an exemplary embodiment, an aloe vera extract may have a concentration between about 0.1 wt. % and about 25 wt. % of dry weight of the wound dressing.

In an exemplary embodiment, a calendula extract may have a concentration up to about 15 wt. % of dry weight of the wound dressing. In an exemplary embodiment, a peppermint extract may have a concentration up to about 1 wt. % of dry weight of the wound dressing. In an exemplary embodiment, olive oil may have a concentration up to about 15 wt. % of dry weight of the wound dressing. In an exemplary embodiment, an exemplary wound dressing may further include water with a weight ratio of at least about 80 wt. % of total weight of the wound dressing.

FIG. 1 illustrates a flowchart of an exemplary method 100 for fabricating an exemplary wound dressing containing a plurality of thymol nanoparticles, consistent with one or more exemplary embodiments of the present disclosure. An exemplary method 100 may include producing a plurality of thymol nanoparticles (step 102), forming a first mixture by mixing the plurality of thymol nanoparticles with biopolymers (step 104), forming a second mixture containing a crosslinking agent (step 106), mixing the first mixture and the second mixture (step 108).

Figure 2:
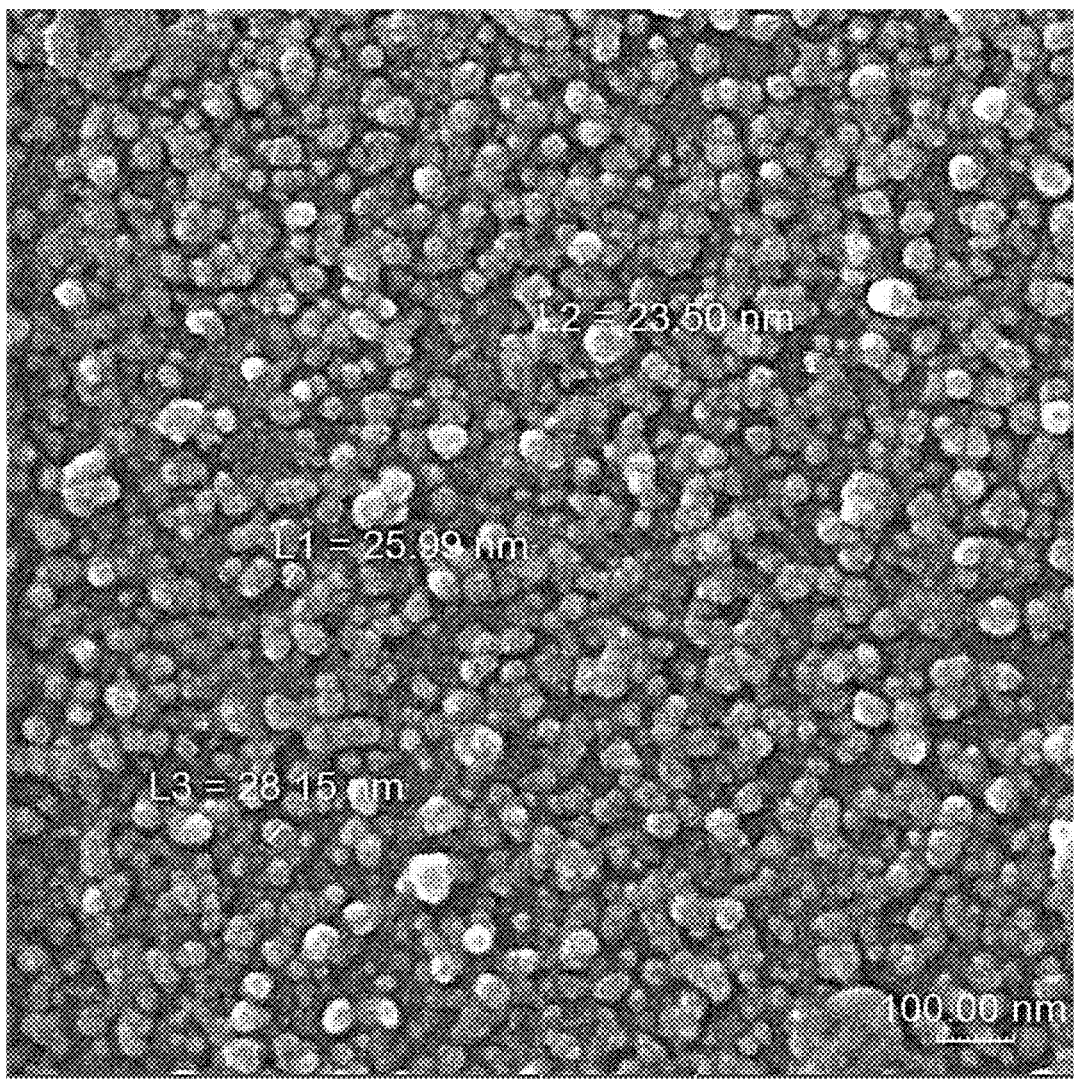
FIG. 2 illustrates a field emission scanning electron microscopy (FESEM) image of a plurality of thymol nanoparticles, consistent with one or more exemplary embodiments of the present disclosure.

In further detail with respect to step 102, in an exemplary embodiment, producing a plurality of thymol nanoparticles may include nanosizing a plurality of thymol particles using a ball mill or a propeller mill. The plurality of thymol particles may be obtained by purifying essential oil of *Zataria multiflora*. The essential oil of *Zataria multiflora* may be obtained through hydro-distillation using an industrial-grade Clevenger-type apparatus. In an exemplary embodiment, Thymol may be the main antimicrobial and antioxidant substance of *Zataria multiflora*. FIG. 2 illustrates a field emission scanning electron microscopy (FE-SEM) image of a plurality of thymol nanoparticles, consistent with one or more exemplary embodiments of the present disclosure. In an exemplary embodiment, the plurality of thymol nanoparticles displayed in FIG. 2 may be produced using a process analogous to step 102. Referring to FIG. 2, the plurality of thymol nanoparticles had a particle size between about 1 nm and about 100 nm, particularly between about 20 nm and about 30 nm.

In further detail with respect to step 104, in an exemplary embodiment, forming a first mixture by mixing a suspension of the plurality of thymol nanoparticles with a biopolymer solution may include mixing the suspension of the plurality of thymol nanoparticles with a biopolymer solution of gelatin, chitosan, PVP, and CMC. At first, the biopolymer solution may be prepared by dissolving gelatin, chitosan, PVP, and CMC in water at a temperature of about 50° C. in an industrial mixer.

Since thymol is a phenolic, crystalline monoterpene, the plurality of thymol nanoparticles may not soluble in water; as a result, the suspension of the plurality of thymol nanoparticles may be prepared by homogenizing the plurality of thymol nanoparticles in water using an ultrasonic homogenizer. After the complete dissolution of the biopolymers in water, the first mixture may be formed by adding the suspension of the plurality of thymol nanoparticles, honey, glycerin, and ATP to the biopolymer solution.

In further detail with respect to step 106, in an exemplary embodiment, forming a second mixture containing a crosslinking agent may include forming the second mixture by mixing a vitamin C solution with genipin. Exemplary genipin may be obtained using an extract of garden-variety jasmine (*Gardenia jasminoides*). Exemplary vitamin C solution may be formed by dissolving vitamin in cold water. The second mixture may also include other herbal extracts such as at least one of a chamomile extract, an aloe vera extract, a calendula extract, a peppermint extract, and olive oil.

In further detail with respect to step 108, in an exemplary embodiment, mixing the first mixture and the second mixture may include forming a final mixture by combining the first mixture and the second mixture using a mixture. After mixing the first mixture and the second mixture, the final mixture may be injected into several molds of the exemplary wound dressing.

Example 1: An Exemplary Wound Dressing Containing Thymol Nanoparticles for Treating Bedsores An exemplary wound dressing specialized for treating bedsores may include a plurality of thymol nanoparticles with a concentration between about 0.01 wt. % and about 1 wt. % of dry weight of the wound dressing loaded into a hydropolymer matrix crosslinked using genipin. An exemplary wound dressing specialized for treating bedsores may also include vitamin C with a concentration between about 0.001 wt. % and about 1 wt. % of dry weight of the wound dressing, ATP with a concentration between about 0.0001 wt. % and about 0.1 wt. % of dry weight of the wound dressing, honey with a concentration between about 5 wt. % and about 25 wt. % of dry weight of the wound dressing, glycerin with a concentration between about 5 wt. % and about 25 wt. % of dry weight of the wound dressing, a chamomile extract with a concentration up to about 15% of dry weight of the wound dressing, an aloe vera extract with a concentration between about 0.1% and about 25% of dry weight of the wound dressing, a peppermint extract with a concentration up to about 1 wt. % of dry weight of the wound dressing, An exemplary hydropolymer matrix may include gelatin with a concentration between about 10 wt. % and about 90 wt. % of dry weight of the wound dressing, chitosan with a concentration between about 0.1 wt. % and about 30 wt. % of dry weight of the wound dressing, PVP with a concentration between about 1 wt. % and about 10 wt. % of dry weight of the wound dressing, and CMC with a concentration between about 0.1 wt. % and about 35 wt. % of dry weight of the wound dressing. The genipin may have a concentration between about 1 wt. % and about 20 wt. % of dry weight of the wound dressing.

Example 2: An Exemplary Wound Dressing Containing Thymol Nanoparticles for Treating Burn Wounds An exemplary wound dressing specialized for treating burn wounds may include a plurality of thymol nanoparticles with a concentration between about 0.01 wt. % and about 1 wt. % of dry weight of the wound dressing loaded into a hydropolymer matrix crosslinked using genipin. An exemplary wound dressing specialized for treating bedsores also includes vitamin C with a concentration between about 0.001 wt. % and about 1 wt. % of dry weight of the wound dressing, ATP with a concentration between about 0.0001 wt. % and about 0.1 wt. % of dry weight of the wound dressing, honey with a concentration between about 5 wt. % and about 25 wt. % of dry weight of the wound dressing, glycerin with a concentration between about 5 wt. % and about 25 wt. % of dry weight of the wound dressing, an aloe vera extract with a concentration between about 0.1% and about 25% of dry weight of the wound dressing, olive oil with a concentration up to about 15 wt. % of dry weight of the wound dressing, and a calendula extract with a concentration up to about 15 wt. % of dry weight of the wound dressing.

An hydropolymer matrix may include gelatin with a concentration between about 10 wt. % and about 90 wt. % of dry weight of the wound dressing, chitosan with a concentration between about 2 wt. % and about 30 wt. % of dry weight of the wound dressing, PVP with a concentration between about 1 wt. % and about 10 wt. % of dry weight of the wound dressing, and CMC with a concentration between about 0.1 wt. % and about 35 wt. % of dry weight of the wound dressing. Exemplary genipin may have a concentration between about 1 wt. % and about 20 wt. % of dry weight of the wound dressing.

Example 3: An Exemplary Wound Dressing Containing Thymol Nanoparticles for Treating Diabetic Ulcers An exemplary wound dressing specialized for treating diabetic ulcers may include a plurality of thymol nanoparticles with a concentration between about 0.01 wt. % and about 1 wt. % of dry weight of the wound dressing loaded into a hydropolymer matrix crosslinked using genipin. An exemplary wound dressing specialized for treating bedsores may also include vitamin C with a concentration between about 0.001 wt. % and about 1 wt. % of dry weight of the wound dressing, ATP with a concentration between about 0.0001 wt. % and about 0.1 wt. % of dry weight of the wound dressing, honey with a concentration between about 1 wt. % and about 20 wt. % of dry weight of the wound dressing, glycerin with a concentration between about 5 wt. % and about 25 wt. % of dry weight of the wound dressing, an aloe vera extract with a concentration between about 0.1% and about 25% of dry weight of the wound dressing, olive oil with a concentration up to about 5 wt. % of dry weight of the wound dressing, and a chamomile extract with a concentration up to about 15 wt. % of dry weight of the wound dressing, and a calendula extract with a concentration up to about 15 wt. % of dry weight of the wound dressing.

Exemplary hydropolymer matrix may include gelatin with a concentration between about 10 wt. % and about 90 wt. % of dry weight of the wound dressing, chitosan with a concentration between about 2 wt. % and about 30 wt. % of dry weight of the wound dressing, PVP with a concentration between about 1 wt. % and about 10 wt. % of dry weight of the wound dressing, and CMC with a concentration between about 0.1 wt. % and about 35 wt. % of dry weight of the wound dressing. The genipin has a concentration between about 1 wt. % and about 20 wt. % of dry weight of the wound dressing.

Figure 3:
FIG. 3 illustrates images of wound healing processes of different patients using an exemplary wound dressing, consistent with one or more exemplary embodiments of the present disclosure.
Figure 3:
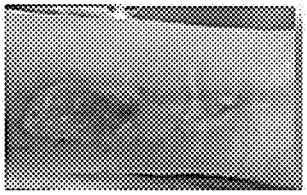
Figure 3:
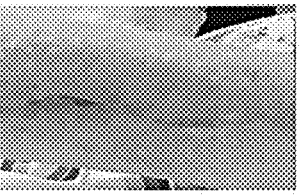
Figure 3:
Figure 3:
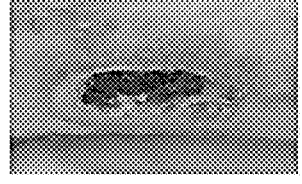
Figure 3:
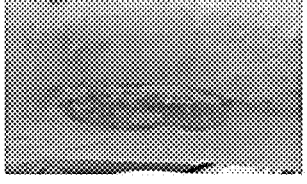
Figure 3:
Figure 3:
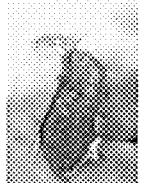
Figure 3:
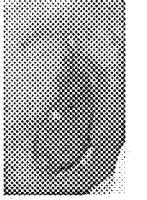
Figure 3:
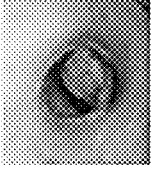
Figure 3:
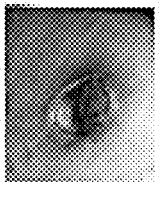
Figure 3:
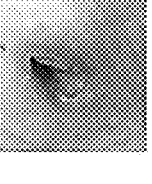

Example 4: Wound Treatment Using an Exemplary Wound Dressing Containing Thymol Nanoparticles In this example, wound treatment using the exemplary wound dressing was examined by using an exemplary wound dressing for different patients. FIG. 3 illustrates images of wound healing processes of different patients using an exemplary wound dressing in 30 days, consistent with one or more exemplary embodiments of the present disclosure. In detail, FIG. 3 illustrates images of respective wound sites for four patients on the first day they were provided treatment (right before treatment, "Day 0"), on the fifteen day after the dressing was utilized at the respective wound site ("Day 15"), and on the thirtieth day after the dressing was utilized at the respective wound site ("Day 30"). Referring to FIG. 3, patient 1 was a 91-year-old woman with a grade three (3) bedsore in her left leg. The bedsore was a necrotic wound with a size of about 4 cm by 12 cm with a bad odor because of an infection of the wound site. After using an exemplary wound dressing, the wound healing process was observed over a period of time. The Day 30 result of patient 1 was significantly acceptable in terms of healing considering the old age and physical condition of the patient.

Patient 2 was also a 91-year-old woman with a grade three (3) bedsore in her right leg. The bedsore was a necrotic wound with a size of about 7 cm by 10 cm with a bad smell because of an infection of the wound site. The bedsore was also expanding and had bleeding. After using an exemplary wound dressing, the bedsore was healed about 70% after 30 days. As a result, the Day 30 result of patient 2 was significantly acceptable in terms of healing considering the old age and physical condition of the patient.

Patient 3 was also a 93-year-old woman with a grade three (3) bedsore in her back. The bedsore had a size of about 8 cm by 21 cm with a bad odor because of an infection of the wound site. The Day 30 result of patient 3 was acceptable in terms of healing considering the old age and physical condition of the patient.

Also, patient 4 was also a 93-year-old woman with a cavity wound caused by a femoral fracture. The wound has a size of about 4 cm*4 cm and a depth of about 5 cm with a bad smell because of an infection of the wound site. After using an exemplary wound dressing, the wound healing process was observed over a period of time. The Day 30 result of patient 1 was significantly acceptable in terms of healing considering the old age and physical condition of the patient.

Example 5: Biocompatibility Assays of an Exemplary Wound Dressing Containing Thymol Nanoparticles In this example, cytotoxicity, sensitivity, and irritability effects of an exemplary wound dressing were examined. Cytotoxicity effect of an exemplary wound dressing was evaluated in a 3-(4, 5-dimethylthiazol-2-yl)-2, 5-diphenyltetrazolium bromide (MTT) assay. At first, an extract of an exemplary wound dressing was prepared by immersing an exemplary wound dressing in complete RPMI medium for 7 days in a $CO_2$ incubator at a temperature of about 37° C. The amount of the complete RPMI medium was about 0.1 ml per 0.6 $cm^2$ of a cross-section of an exemplary wound dressing. The fibroblast cells of the L929 cell line then were seeded into a 96-well flat-bottomed plate.

In a test group, fibroblast cells were cultured in contact with the extract of an exemplary wound dressing. In a control group, fibroblast cells were cultured without the extract of an exemplary wound dressing. In the end, viability of the fibroblast cells was examined 24 hours after the culture. According to the MTT assay, the viability of the fibroblast cells of the test group was about 95% of the control group; therefore, the exemplary wound dressing had no cytotoxicity and concentrations of compounds released from the exemplary wound dressing were not in the cytotoxic ranges.

It is well-established that suitable preclinical studies before starting a clinical trial in humans are pivotal to obtain high-quality data and avoid possible side effects. Major goals of preclinical tests for wound dressing are evaluating irritability and sensitivity of the wound dressing on animals such as mice and rabbits. In order to evaluate irritability of the exemplary wound dressing, a scratch was made on the back of a New Zealand white rabbit and an exemplary wound dressing and a control sample were placed in the scratch site for about 24 hours. After 24 hours, the scratch site was examined regarding the presence of edema and erythema. According to the results, the exemplary wound dressing utilized in the trial caused no erythema and edema in comparison with the control sample.

Furthermore, in order to examine the sensitivity effect of an exemplary wound dressing, a scratch was made on the back of an albino guinea pig and an extract of an exemplary wound dressing was administered to the scratch site by intradermal injection of 0.1 ml of the extract of the exemplary wound dressing. After two weeks, the injection site was examined regarding the presence of edema and erythema. Result of the sensitivity assay indicates that the exemplary wound dressing utilized on the albino guinea pig had no sensitivity effect.

Example 8: Antibacterial and Antioxidant Activity of an Exemplary Wound Dressing Containing Thymol Nanoparticles In this example, an antibacterial activity of an exemplary wound dressing was investigated against *Staphylococcus aureus, Escherichia coli, Pseudomonas aeruginosa*, and *Enterococcus hirae* using disk diffusion method. In the disk diffusion method, an inhibition zone diameter was measured to determine the antibacterial activity of different formulations. In order to determine antibacterial activity of an exemplary wound dressing, a sample of the exemplary wound dressing with a diameter of about 10 cm was placed on the surface of nutrient agar inoculated with a bacterial suspension and incubated overnight at a temperature of about 37° C. In the end, a clear area around each sample was determined as a zone of inhibition. TABLE. 1 represents inhibition zone diameters of the exemplary wound dressing against different bacteria with an acceptable to moderate antibacterial activity.

TABLE 1

Inhibition zone diameter of the exemplary wound dressing against different bacteria

| Bacteria | Sample diameter | Total diameter after culture | Inhibition zone diameter (mm) | Antibacterial activity |
|---|---|---|---|---|
| *Staphylococcus aureus* | 10 | 11 | 0.5 | Acceptable |
| *Escherichia coli* | 10 | 11 | 0.5 | Acceptable |
| *Pseudomonas aeruginosa* | 10 | 10.5 | 0.25 | Moderate |
| *Enterococcus hirae* | 10 | 11 | 0.5 | Acceptable |

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A wound dressing, comprising:
a hydropolymer matrix crosslinked with genipin, the hydropolymer matrix comprising:
   gelatin with a concentration between 10 wt. % and 90 wt. % of dry weight of the wound dressing;
   chitosan with a concentration between 0.1 wt. % and 30 wt. % of dry weight of the wound dressing;
   polyvinylpyrrolidone (PVP) with a concentration between 0.1 wt. % and 10 wt. % of dry weight of the wound dressing; and
   carboxymethyl cellulose (CMC) with a concentration between 0.1 wt. % and 35 wt. % of dry weight of the wound dressing;
a plurality of thymol nanoparticles with a concentration between 0.01 wt. % and 1 wt. % of dry weight of the wound dressing, the plurality of thymol nanoparticles loaded into the hydropolymer matrix;
adenosine triphosphate (ATP) with a concentration between 0.0001 wt. % and 0.1 wt. % of dry weight of the wound dressing;
vitamin C with a concentration between 0.001 wt. % and 1 wt. % of dry weight of the wound dressing; and
honey with a concentration between 5 wt. % and 25 wt. % of dry weight of the wound dressing.

2. A wound dressing, comprising:
a hydropolymer matrix crosslinked with genipin, the hydropolymer matrix comprising gelatin, chitosan, polyvinylpyrrolidone (PVP), and carboxymethyl cellulose (CMC); and
a plurality of thymol nanoparticles with a concentration between 0.01 wt. % and 1 wt. % of dry weight of the wound dressing, the plurality of thymol nanoparticles loaded into the hydropolymer matrix.

3. The wound dressing of claim 2, wherein the hydropolymer matrix comprises the gelatin with a concentration between 10 wt. % and 90 wt. % of dry weight of the wound dressing.

4. The wound dressing of claim 2, wherein the hydropolymer matrix comprises the chitosan with a concentration between 0.1 wt. % and 30 wt. % of dry weight of the wound dressing.

5. The wound dressing of claim 2, wherein the hydropolymer matrix comprises the PVP with a concentration between 0.1 wt. % and 10 wt. % of dry weight of the wound dressing.

6. The wound dressing of claim 2, wherein the hydropolymer matrix comprises the CMC with a concentration between 0.1 wt. % and 35 wt. % of dry weight of the wound dressing.

7. The wound dressing of claim 2, wherein the wound dressing comprises the genipin with a concentration between 1 wt. % and 20 wt. % of dry weight of the wound dressing.

8. The wound dressing of claim 2, wherein each of the plurality of thymol nanoparticles has a particle size between 20 nm and 30 nm.

9. The wound dressing of claim 2 further comprises adenosine triphosphate (ATP).

10. The wound dressing of claim 9, wherein the ATP has a concentration between 0.0001 wt. % and 0.1 wt. % of dry weight of the wound dressing.

11. The wound dressing of claim 2 further comprises vitamin C.

12. The wound dressing of claim 11, wherein the vitamin C has a concentration between 0.001 wt. % and 1 wt. % of dry weight of the wound dressing.

13. The wound dressing of claim 2 further comprises honey.

14. The wound dressing of claim 13, wherein the honey has a concentration between 5 wt. % and 25 wt. % of dry weight of the wound dressing.

15. The wound dressing of claim 2 further comprises glycerin.

16. The wound dressing of claim 15, wherein the glycerin has a concentration between 5 wt. % and 25 wt. % of dry weight of the wound dressing.

17. The wound dressing of claim 2 further comprises an additive, the additive comprising at least one of a chamomile extract, an aloe vera extract, a calendula extract, a peppermint extract, and olive oil.

18. The wound dressing of claim 17, wherein the additive comprises at least one of:
  a chamomile extract with a concentration up to 15 wt. % of dry weight of the wound dressing;
  an aloe vera extract with a concentration between 0.1 wt. % and 25 wt. % of dry weight of the wound dressing;
  a calendula extract with a concentration up to 15 wt. % of dry weight of the wound dressing;
  a peppermint extract with a concentration up to 1 wt. % of dry weight of the wound dressing; and
  olive oil with a concentration up to 15 wt. % of dry weight of the wound dressing.

19. The wound dressing of claim 2 further comprising water with a weight ratio of at least 80 wt. % of total weight of the wound dressing.

\* \* \* \* \*